Figure 1:
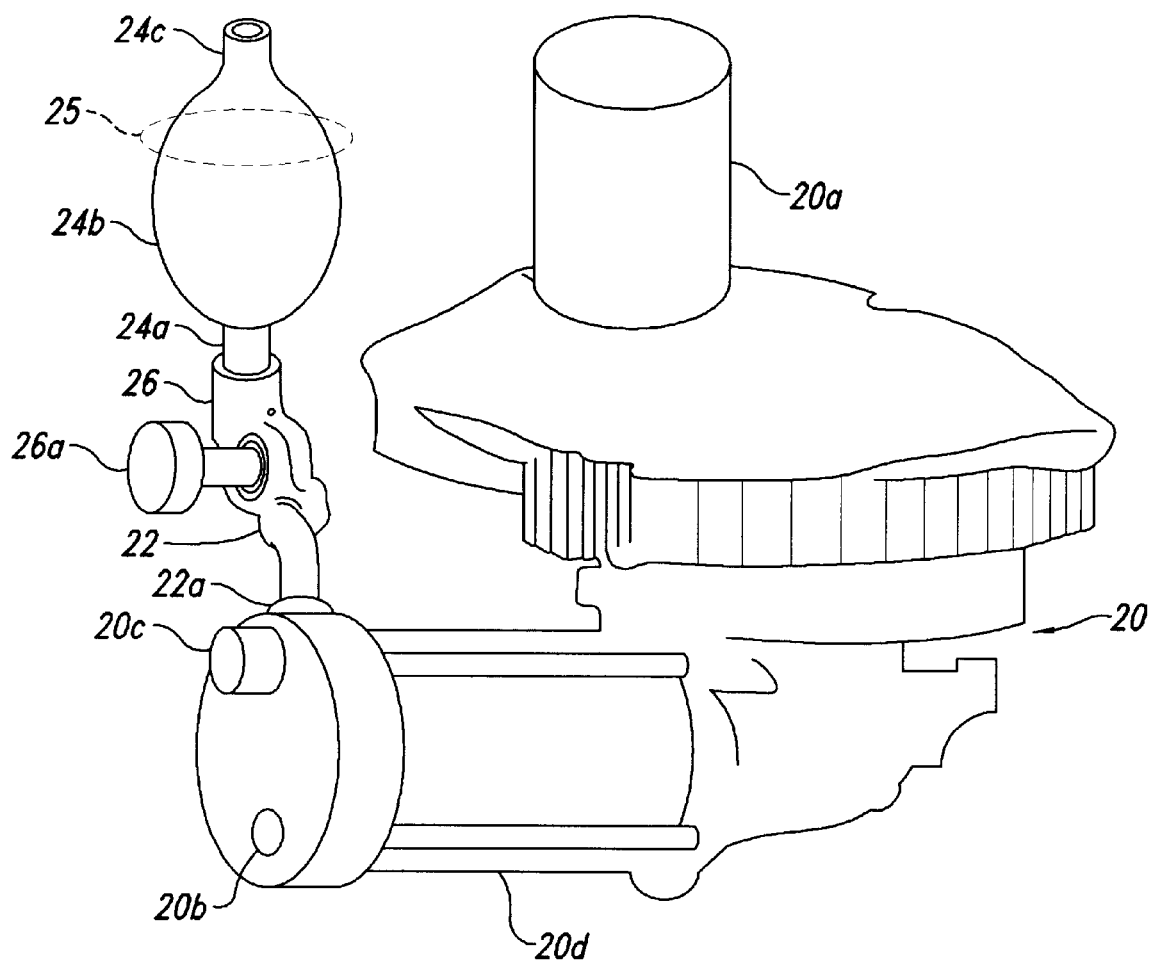
Figure 2A:
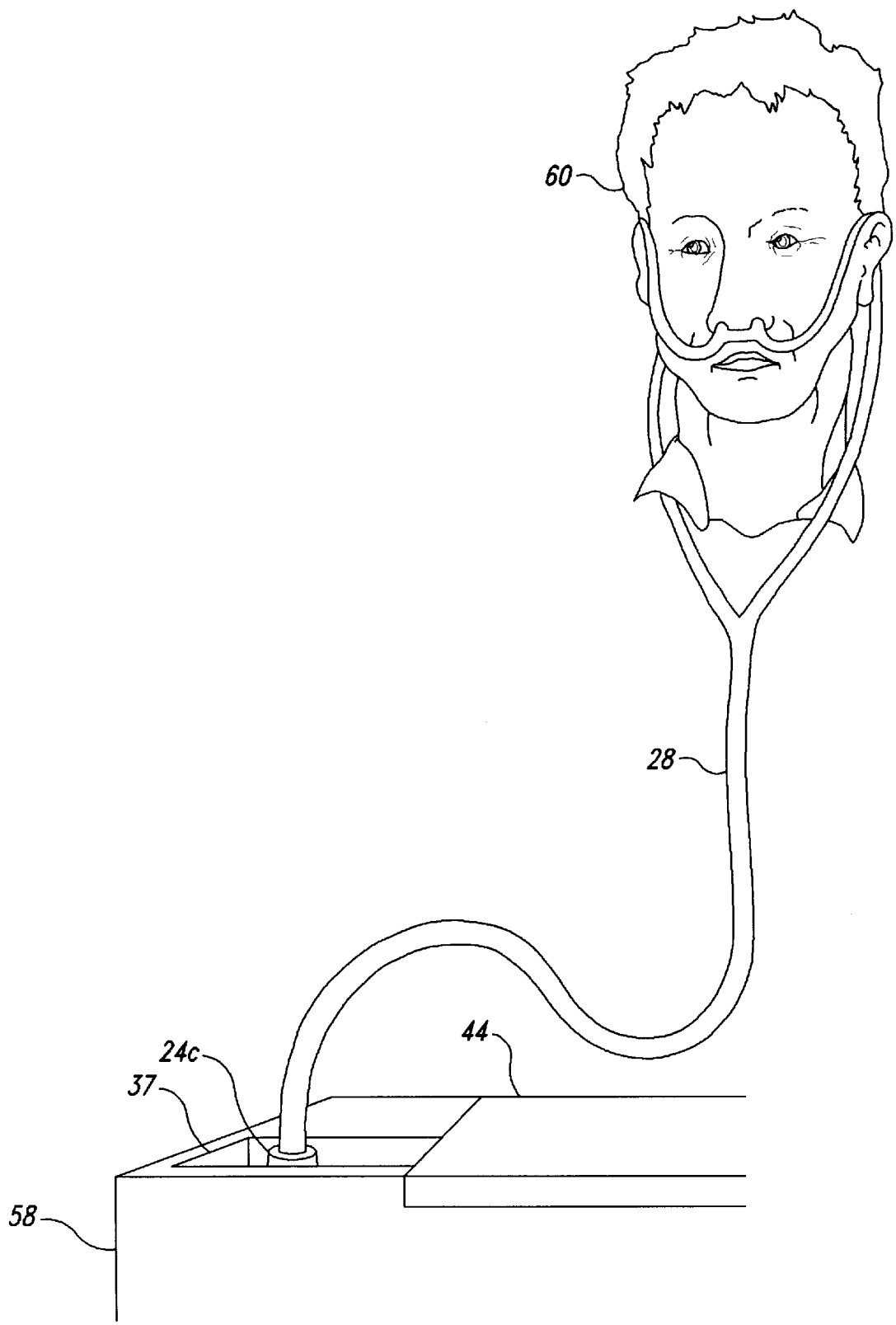
Figure 2B:
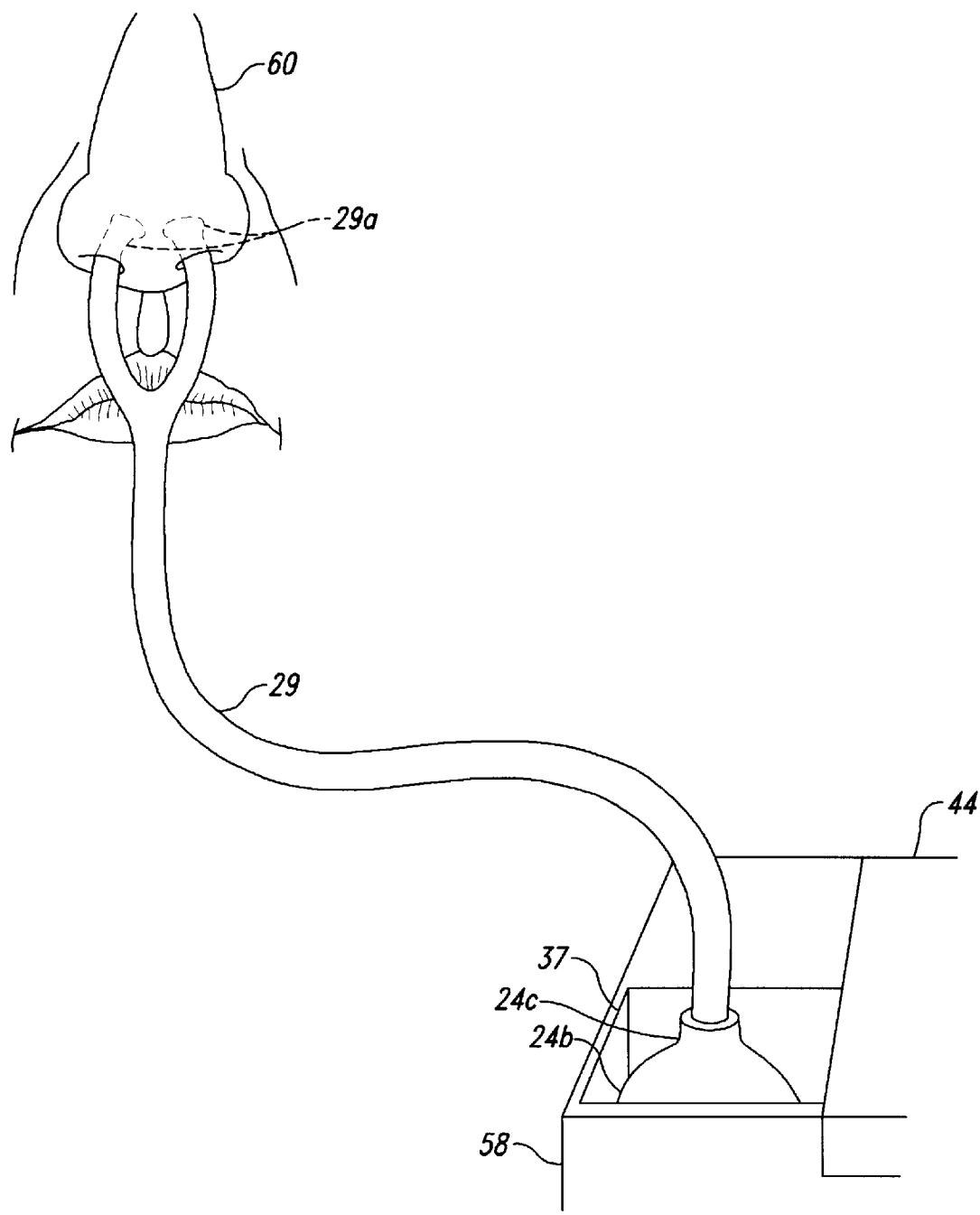
Figure 2C:
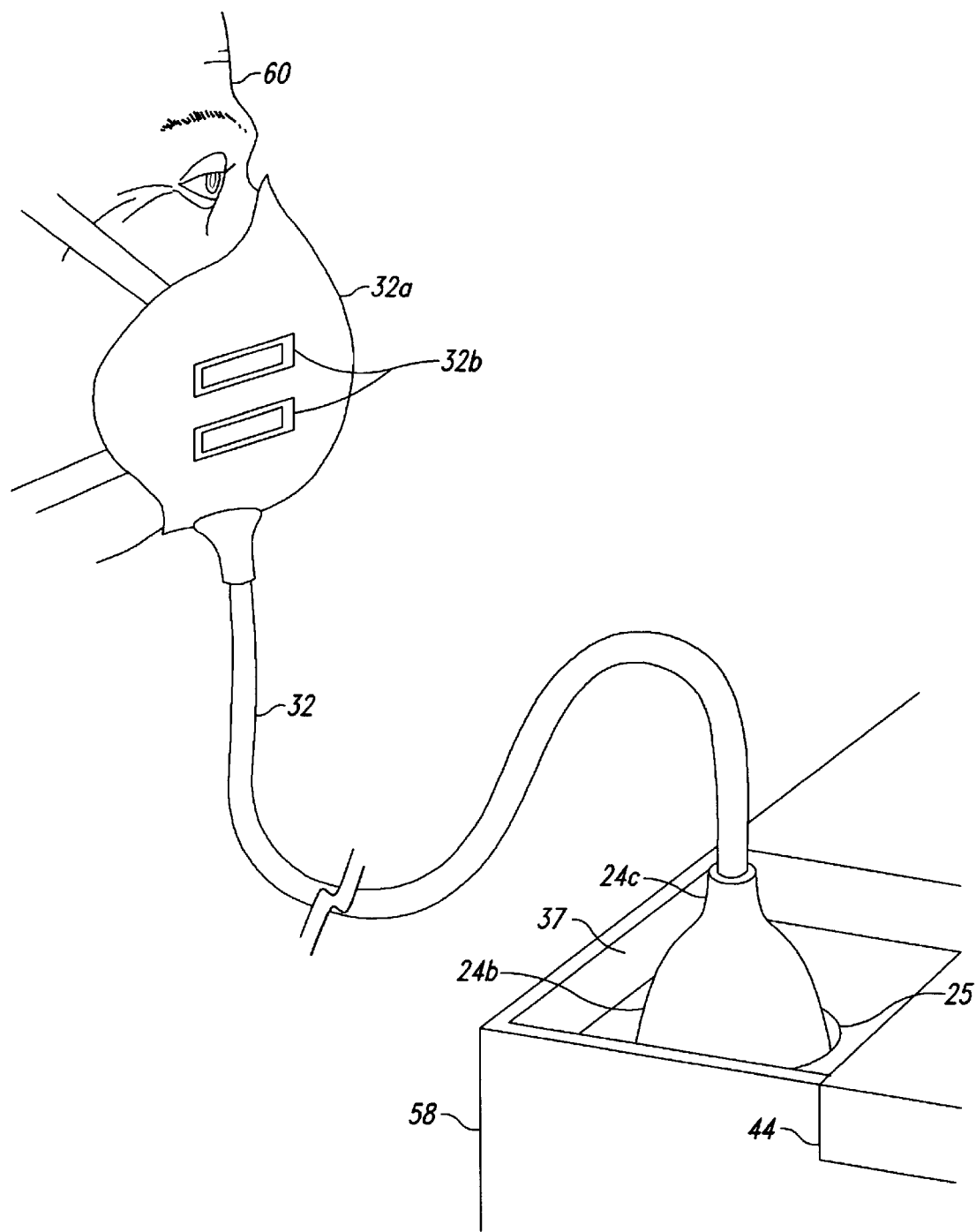
Figure 2D:
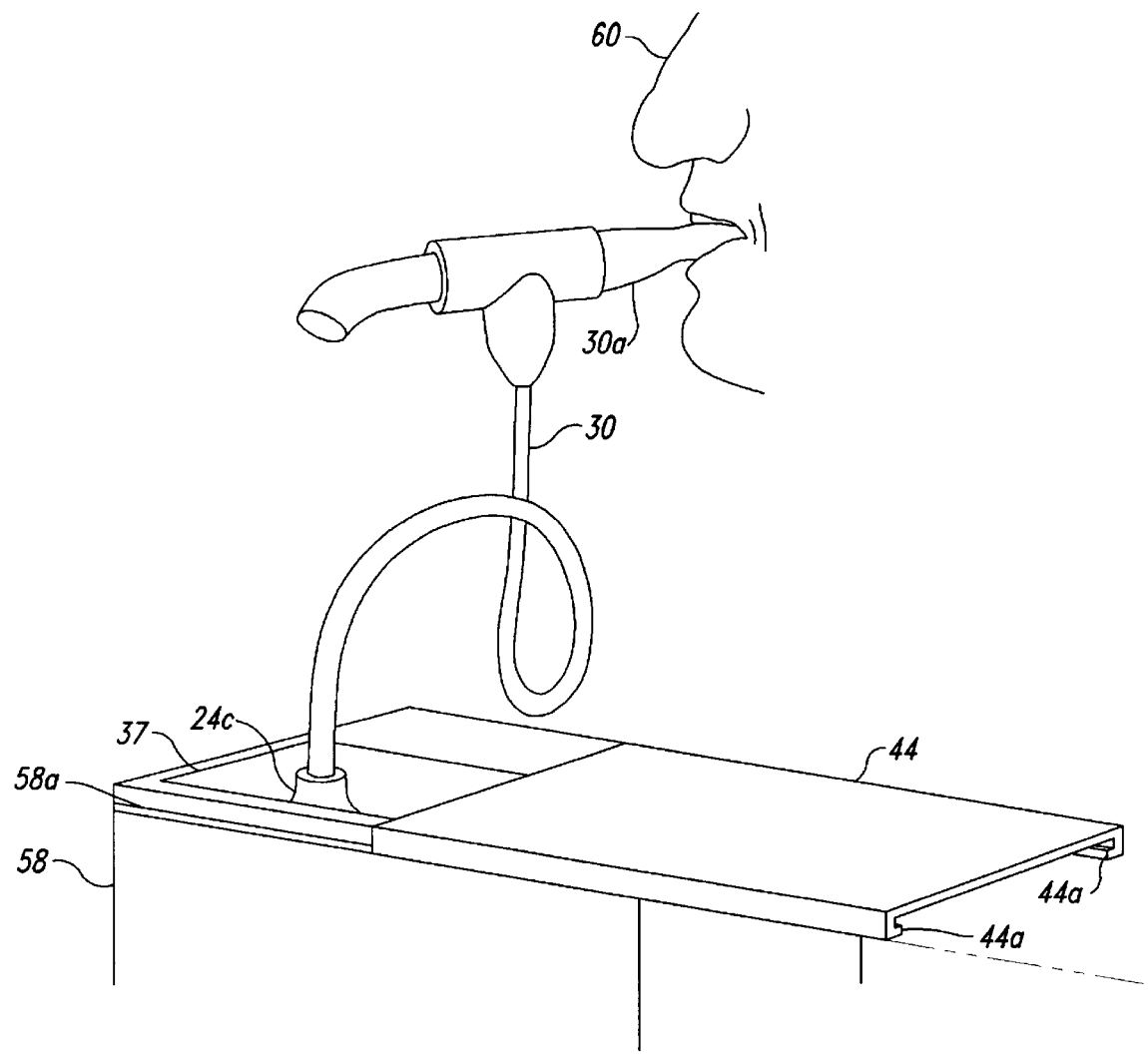

United States Patent [19]
Cooper

[11] Patent Number: 6,076,520
[45] Date of Patent: Jun. 20, 2000

[54] DEVICE FOR NASAL THERAPEUTIC INHALATION

[76] Inventor: Emily L. Cooper, 17595 Vierra Canyon Rd., Box 158, Salinas, Calif. 93907

[21] Appl. No.: 08/854,553

[22] Filed: May 12, 1997

[51] Int. Cl.[7] .................................................. A61M 11/00
[52] U.S. Cl. ............................. 128/200.21; 128/200.14; 128/207.18; 128/203.12; 128/205.22
[58] Field of Search ..................... 128/205.25, 205.27, 128/204.18, 207.18, 200.24, 200.16, 203.12, 200.14

[56] References Cited

U.S. PATENT DOCUMENTS

| | | | |
|---|---|---|---|
| 759,152 | 5/1904 | Bennett | 128/207.18 |
| 1,105,934 | 8/1914 | Stevens | 128/204.13 |
| 3,581,742 | 6/1971 | Glenn | 128/200.14 |
| 3,584,621 | 6/1971 | Bird | 128/200.14 |
| 3,902,486 | 9/1975 | Guichard . | |
| 4,244,361 | 1/1981 | Neubert | 128/200.14 |
| 4,257,415 | 3/1981 | Rubin . | |
| 4,273,124 | 6/1981 | Zimmerman | 128/207.18 |
| 4,343,304 | 8/1982 | Hickmann | 128/200.14 |
| 4,403,611 | 9/1983 | Babbittt et al. | 604/73 |
| 4,602,644 | 7/1986 | DiBenedetto et al. | 128/725 |
| 4,648,398 | 3/1987 | Agdanowski et al. | 128/207.18 |
| 4,685,456 | 8/1987 | Smart | 128/205.22 |
| 4,753,233 | 6/1988 | Grimes | 128/207.18 |
| 4,823,784 | 4/1989 | Bordini . | |
| 5,022,587 | 6/1991 | Hochstein . | |
| 5,170,782 | 12/1992 | Kocinski | 128/200 |
| 5,224,471 | 7/1993 | Marelli et al. | 128/200.14 |
| 5,250,287 | 10/1993 | Cocozza | 424/45 |
| 5,299,565 | 4/1994 | Brown . | |
| 5,348,000 | 9/1994 | Teves | 128/204.18 |
| 5,443,059 | 8/1995 | Koch et al. | 128/200.16 |
| 5,508,269 | 4/1996 | Smith et al. | 514/38 |
| 5,511,726 | 4/1996 | Greenspan . | |
| 5,549,102 | 8/1996 | Lintl et al. | 128/200.21 |
| 5,551,416 | 9/1996 | Stimpson et al. | 128/200.16 |
| 5,570,682 | 11/1996 | Johnson | 128/200.14 |
| 5,582,164 | 12/1996 | Sanders | 128/205.22 |
| 5,584,285 | 12/1996 | Salter et al. | 128/200.21 |
| 5,595,174 | 1/1997 | Gwaltney | 128/201.15 |
| 5,611,332 | 3/1997 | Bono | 128/200.18 |

FOREIGN PATENT DOCUMENTS

| | | | |
|---|---|---|---|
| 0 504 509 A1 | 9/1992 | European Pat. Off. . | |
| 0 712 636 A1 | 5/1996 | European Pat. Off. . | |
| 0712636A1 | 5/1996 | European Pat. Off. | 128/200.14 |
| 2 358 932 | 2/1978 | France . | |
| WO 97/18752 | 5/1997 | WIPO | 128/204.18 |

OTHER PUBLICATIONS

Cummings, Charles, W., et al, eds, *Otolaryngology Head & Neck Surgery,* Mosby–Year Book, Inc., St. Louis, Missouri, 1998, Chap. 55, "Anatomy," pp. 1059–1064.

Netter, Frank H., M.D., "Interactive Atlas Of Human Anatomy," (CD–ROM), ©1995, Novartis, DxR Development Group, Inc.

(List continued on next page.)

*Primary Examiner*—Aaron J. Lewis
*Assistant Examiner*—Joseph F. Weiss, Jr.
*Attorney, Agent, or Firm*—Perkins Coie LLP

[57] ABSTRACT

A nasal inhalation device for nebulizing liquid, including medication, used in treatment of upper respiratory and other conditions amenable to intra-nasal administration of medication. Comprises an internal, electrically powered air compressor unit, a nebulizing device, a conduit for connecting the air compressor to nebulizing device and tubing for delivering nebulized fluid to an individual's nasal passages. The compressor unit produces a pressurized air flow which passes through the connecting conduit to the nebulizing means. In the nebulizing device the pressurized air flow interacts with liquid and medication to reduce it to a fine spray. The tubing means carries the spray into individual's nasal passages to effect inhalation therapy for nasal and upper respiratory conditions and for a variety of other conditions whose treating medications have an intra-nasal route of administration.

24 Claims, 12 Drawing Sheets

OTHER PUBLICATIONS

Hannallah, M.S., et al. "The relationship between left mainstem bronchial diameter and patient size," *J. Cardiotharac Vasc. Anesth,* Apr. 1995, 9(2):119–21. (Abstract only).

Johnson, Eric P, ed., *ACSM's Resource Manual for Guidelines For Exercise Testing And Prescription,* Williams & Wilkins, (Third Edition), 1998, Chap. 36, "Pulmonary Adaptations to Dynamic Exercise" pp. 309–319.

Nunn, J.F., *Nunns Applied Respiratory Physiology,* Butterworth–Heinemann Ltd., Oxford, (Fourth Edition), 1993, Chapter 14.

Hollinshead, W. Henry, *Anatomy for Surgeons, vol. 1: The Head & Neck,* Harper & Row Publishers, Inc., (Third Edition) 1982, p. 189.

Patent Pending Mefar/Respironics Specification Sheet Feb 17, 1997, Rear Brochure Cover.

DEVICE FOR NASAL THERAPEUTIC INHALATION

BACKGROUND—FIELD OF INVENTION

This invention relates to a nasal therapeutic inhalation device, specifically to such device which is used for providing a stream of nebulized liquid, including medication, to nasal passages of an ambulatory or stationary individual for the treatment of nasal, upper respiratory, and other intra-nasally treated conditions.

BACKGROUND—DESCRIPTION OF PRIOR ART

The sinuses assist in controlling the temperature and humidity of the air that reaches the lungs. The sinuses produce mucus that contains substances capable of destroying bacteria and pollutants from inhaled air before the air reaches the lungs. Conditions that affect nasal passages thus frequently affect the sinuses.

In the treatment of individuals having various respiratory ailments, particularly those having upper respiratory allergic, obstructive and restrictive disease, various methods are used. These include oral, intramuscular, intravenous and intra-nasal methods. There are also a variety of non-respiratory conditions that can be treated by an intra-nasal route.

Noting that nasal administration of liquids and medication is an effective method to alleviate a number of upper respiratory conditions, inventors created several types of hand-held inhalers, actuators, or devices to deliver aqueous and non-aqueous substances directly to the nasal cavities. U.S. Pat. No. 5,224,471 to Marelli (1993) discloses a nasal dispenser for atomized pharmaceutical substances that can deliver nasal medications. U.S. Pat. No. 5,250,287 to Cocozza (1993) discloses a multi-dose insufflator for nasal administration of medicaments.

Such devices are generally difficult to operate. They require positioning the delivery tip of the device in the nostril, simultaneously depressing the triggering mechanism while forcefully inhaling the medication nasally. Furthermore, one is sometimes required to simultaneously restrict air flow to the non-treated nostril. The complexity of administering medications in this form renders them unworkable to those lacking coordination, cooperation or physical ability as in conditions such as arthritis, stroke, children and those with small hands. Accordingly, the devices of the prior art operate such that those with smaller hands, disfiguring arthritis and hand weakness find them awkward to grasp and to operate properly. Such awkwardness limits one's ability to fully depress the actuator. If the actuator is not depressed fully, the medication released is either reduced or absent, rendering the dosage sub-optimal and the treatment ineffective.

Many of the available hand held inhalers of the prior art produce local side effects such as nasal burning, stinging, dryness and irritation. This has presented a significant problem because many conditions being treated with such inhalers involve dry, irritated mucous membranes to begin with. Frequently, an individual prematurely discontinues inhalers due to nosebleeds, excessive dryness, and other side effects. Furthermore, injury and inflammation occasionally occurs due to mechanical trauma from improper insertion of the delivery end of the nasal inhaler into the nostril. According to the American Academy of Family Practice, most cases of local irritation are due to mechanical trauma resulting from improper insertion of the inhaler rather than to direct effects of the medication.

Using aqueous forms of the prior art reduced the side effect of dryness, however, it is sometimes necessary to tilt one's head back, or lay horizontally, then insert the delivery tip into one's nasal cavity, activate the device and inhale through one's nose. A common complaint is of a bitter, unpleasant drainage of medication down the throat. Furthermore, part of the dosage may drip back out the nostril.

In hand held inhalers, the medication is dosed in a bolus form. With each pump, the equivalent of a specific dose and volume of medication is released from the inhaler in the form of a fine spray. Such spray is then deposited within the nasal cavity. Unfortunately, the inhalers carry the spray only to a limited portion of the upper respiratory tract. If tissues are inflamed and obstruct the patency, or cross-sectional diameter of the nostrils, the spray cannot reach higher areas, thereby limiting effectiveness.

Many of the hand-held devices of the prior art are in the form of aerosol sprays that have been found to produce a detrimental effect on the environment. Many such sprays contain gases which deplete the stratospheric ozone layer which shield Earth from ultraviolet radiation. Reformulation of such inhalers is required by law in order to bring the United States into compliance with a 1987 treaty, the 'Montreal Protocol.' The Environmental Protection Agency and the Food and Drug Administration have plans to phase out such devices when alternatives become available. An additional ecological concern is that the canisters used in these units and the dispensers themselves are not recyclable or refillable.

Such inventions of the prior art are expensive to purchase and the contents of such inhalers last an average of about twenty days and therefore must be replaced frequently.

Although prior art devices as shown in U.S. Pat. No. 4,343,304 to Hickmann (1982), and U.S. Pat. No. 4,244,361 to Neubert (1981) deliver nebulized liquid and medication orally to lower respiratory tracts, trachea and lungs, inhalation therapy incorporating nebulized liquid and medication has not been applied nasally to upper respiratory tracts. Furthermore, such devices of the prior art incorporate external nebulizing devices which renders them awkward and cumbersome. In general, there have been no simple devices for providing nebulized treatment to nasal passages or upper respiratory tracts.

Other methods of treating upper respiratory conditions include oral or injectable means of administering medication. Medications in these forms carry potential for systemic, or bodily side effects by their high level of distribution throughout the body where they may not be needed, and only partially reaching and penetrating their target, the upper respiratory tracts where they are needed. Thus there is a need to use higher doses of medication to ensure adequate penetration of target tissue when utilizing these routes of administration.

SUMMARY OF THE INVENTION

Figure 5A:
Figure 5B:
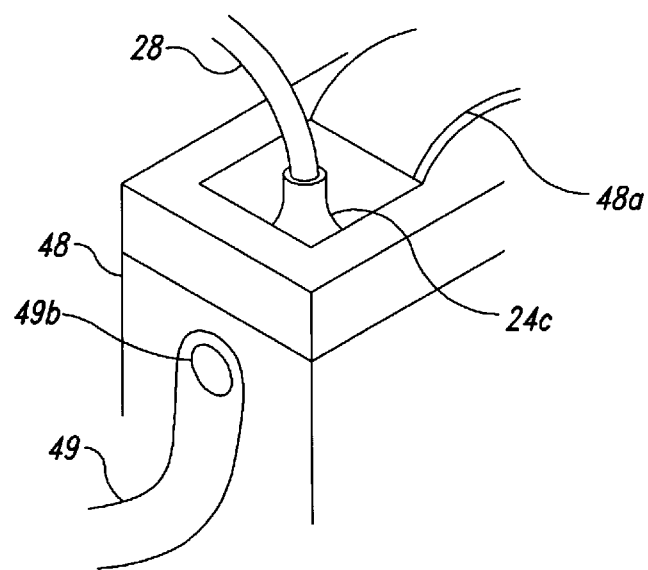
Figure 5D:
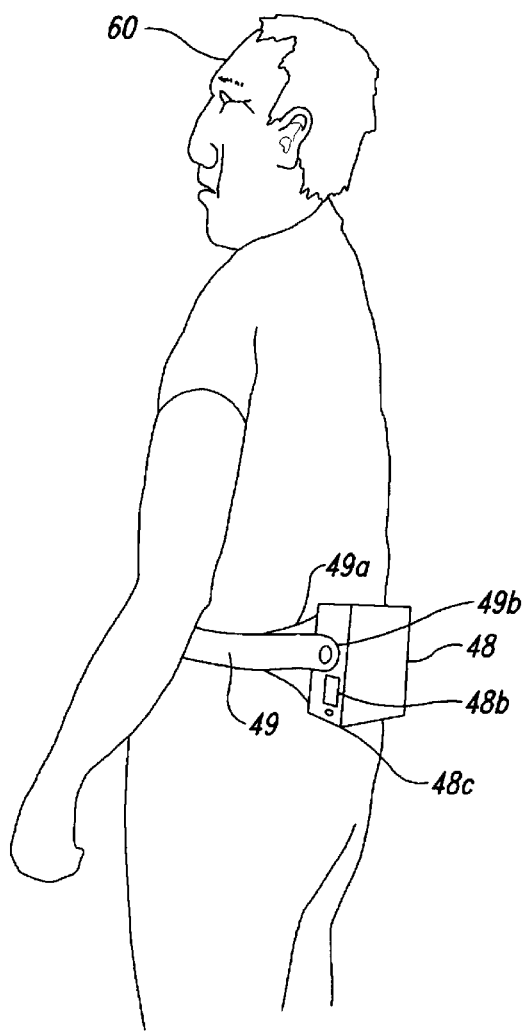
Figure 5C:
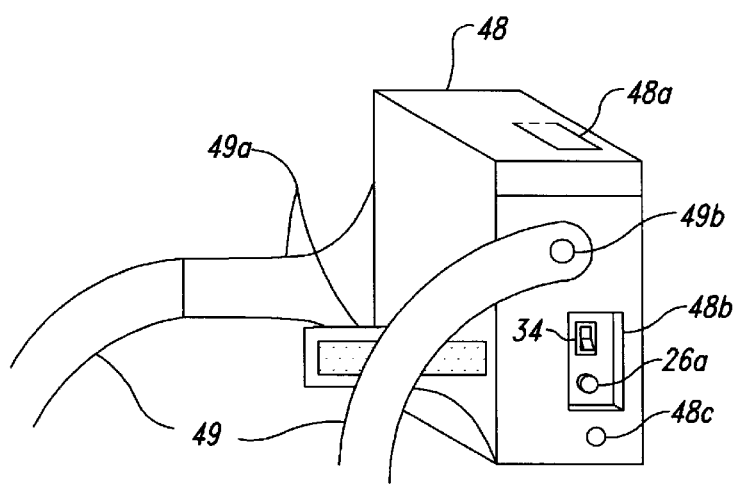
Figure 5E:
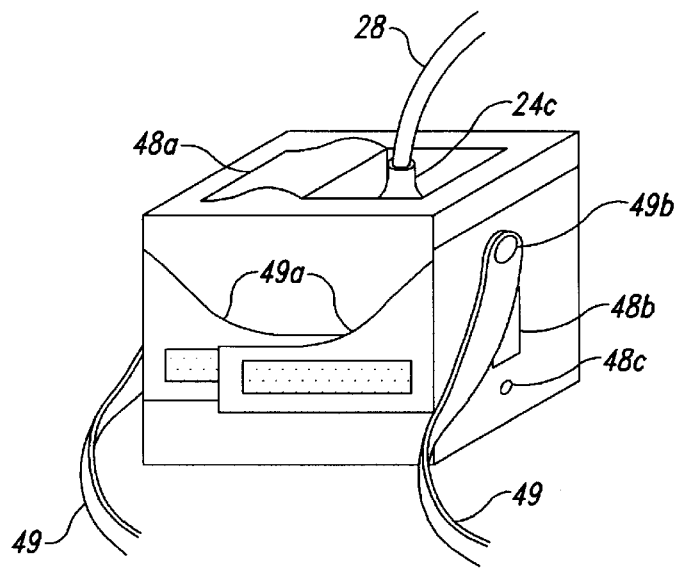

Accordingly, several objects and advantages of my invention are:

(a) to provide a nasal therapeutic inhalation device which is simple to operate and which can be utilized by individuals regardless of age, coordination, hand size or background;

(b) to provide a nasal therapeutic inhalation device which ensures that a predetermined dose has been administered;

(c) to provide a nasal therapeutic inhalation device which will allow the treatment recipient to assume any position whether horizontal or vertical, ambulatory or sedentary;

(d) to provide a nasal therapeutic inhalation device which will provide a greater distribution of inhalant by providing continuous rather than bolus dosing;

(e) to provide a nasal inhalation device for enhancing distribution of treating spray by reducing inflammation, increasing the cross-sectional diameter of the nostrils, thereby allowing more medication to pass through inflammatory obstructions to the upper respiratory tracts;

(f) to provide a nasal therapeutic inhalation device for delivering a continuous spray of liquid and medication consisting of a predetermined particle size, volume and flow rate suited for nasal administration; and (g) to provide a nasal inhalation device for providing treatments directly to the nostrils in order to improve distribution, minimize dosage, thereby minimizing systemic and local side effects.

Other objects and advantages are:

(a) to provide a re-usable, non-disposable nasal inhalation device in keeping with ecological concerns to preserve the ozone layer;

(b) to provide a nasal therapeutic inhalation device which is adaptable to utilize tubing and nebulizing means having minimal packaging and manufactured of recyclable materials;

(c) to provide a nasal inhalation device which will be capable of utilizing a variety of liquids and medications approved by the FDA for nasal administration;

(d) to provide a nasal inhalation device which will be capable of utilizing a variety of liquids and medications currently available and manufactured for nasal administration; and (e) to provide a nasal inhalation device which will be inexpensive to manufacture, purchase and operate.

Further objects and advantages are to provide a re-usable nasal inhalation device which will be comfortable, easy and convenient to use for effective alleviation of a variety of upper respiratory ailments.

Still further objects and advantages will become apparent from a consideration of the drawings and ensuing description.

BRIEF DESCRIPTION OF THE DRAWINGS

FIG. 1 is a perspective view of internal elements of the device including a compressor and a nebulizing device and their attachments.

FIGS. 2A to 2D show various forms of delivery tubing.

FIGS. 3A to 3D show perspective views of the internal and external portions of the shell.

FIG. 4 shows a bottom perspective view showing a removed filter component and a filter compartment.

FIGS. 5A through 5E show carrying methods and carrying case components for the device.

FIG. 6 is a hard-wire diagram showing the relationship of battery 54, switch 34, fail-safe 36, and compressor 20.

In accordance with the present invention the nasal inhalation device is particularly adapted for nasal application of nebulized liquid and medication for the treatment of upper respiratory and other conditions where intra-nasal administration of medication is desired.

DETAILED DESCRIPTION OF THE INVENTION

A typical embodiment of the basic internal elements of the nasal therapeutic inhalation device of the present invention is illustrated in FIG. 1. For purposes of illustration, the outer shell is not shown in FIG. 1. The inhalation device comprises an electrically powered motor 20*a* of a compressor 20 which attaches to a nebulizing device 24 by way of a conduit 22. Conduit 22 attaches to compressor 20 at an inlet 22*a*, and attaches to nebulizing device 24 by at inlet 24*a*. Nebulizing device 24 comprises inlet 24*a*, a reservoir 24*b* and an outlet 24*c*. Position of a ring 25 is indicated by a dashed line and represents the level of nebulizer 24 in relation to shell 58. In the embodiment shown in FIG. 1, the device is equipped with a regulator 26 and a regulator control knob 26*a* interposed between compressor 20 and conduit 22. A Compressor air intake 20*b* and an air output 20c communicate with a pump 20*d*.

In the embodiment shown in FIG. 2A, a nebulizing device outlet 24*c* connects to a nasal tubing 28 which ends in nostrils of individual 60. Also shown is a nebulizer compartment 37 which is part of shell 58. Lid 44 is also sown.

An additional embodiment is shown in FIG. 2B in which an alternate self-retaining nasal tubing 29 and some tubing stays 29*a* are shown.

Shown in FIG. 2C is a further embodiment in which nebulizer outlet 24*c* connects to a face-mask tubing 32 with a mask 32*a*, some vents 32*b*, and individual 60 shown. Also shown is ring 25 and lid 44.

In the embodiment shown in FIG. 2D, nebulizer outlet 24*c* is shown connecting to an oral tubing 30. Also shown is a mouthpiece 30*a*. FIG. 2D also shows lid 44, a lid lip 44*a* and lid acceptance lip 58*a* of shell 58.

FIG. 3A is an upright, front, side perspective view of the enclosed device, showing external case or shell 58. A switch 34, and regulator dial 26*a* are shown. Also shown In FIG. 3A is a lid 44 with a lid lip 44*a*, and a shell lip 58*a* of shell 58. Also shown are lid finger pulls 44*b*. Some air intake openings 27 are also shown.

FIG. 3B is a rear perspective view of the enclosed device showing a tubing storage compartment 38 and a liquid and medication storage compartment 40.

FIG. 3B also shows a removable carrying clip 46. Also shown in FIG. 3B is nebulizing outlet 24*c*. An internal battery compartment 54*c* is also shown.

FIG. 3C is a view showing removable nebulizing device 24 in a partially removed position. Also shown is individual 60 grasping nebulizer outlet 24*c*.

FIG. 3D is a perspective bottom view of the device showing a filter compartment door 43*a* in a closed position. A Battery compartment door 54*a* and some air intake vents 27 are also shown. Switch 34, regulator control 26*a* are shown within a recess 41. Finger pulls 43*b* and 54*b* are also shown.

FIG. 4 is a perspective bottom view of the device with a filter compartment door 43*a* in an open position, showing a removable air filter 42 which fits into a filter compartment 43. Finger pulls 43*b* are also shown.

Additional embodiments are shown in FIG. 5*a* and 5*b*. FIG. 5*a* shows a carrying case 48 and convertible shoulder straps 49 in relation to individual 60. Also shown in FIG. 5A are pivot points 49*b* and a switch access 48*b*.

FIG. 5B shows a close up view of section of case showing nebulizer outlet 24, accessible with a flap 48*a* in an open position and with tubing 28 attached. Switch 34 is accessible through access 48*b*.

FIG. 5C and FIG. 5D show carrying case 48 and an arrangement of convertible straps 49 in relation to individual 60. Also shown are an intake access 48*c*, a nebulizer flap 48a, and switch access 48b. Reversibly adherent fanny conversion straps 49a are shown in open position in FIG. 5C and in closed position for shoulder configuration in FIG. 5E.

Figure 6:
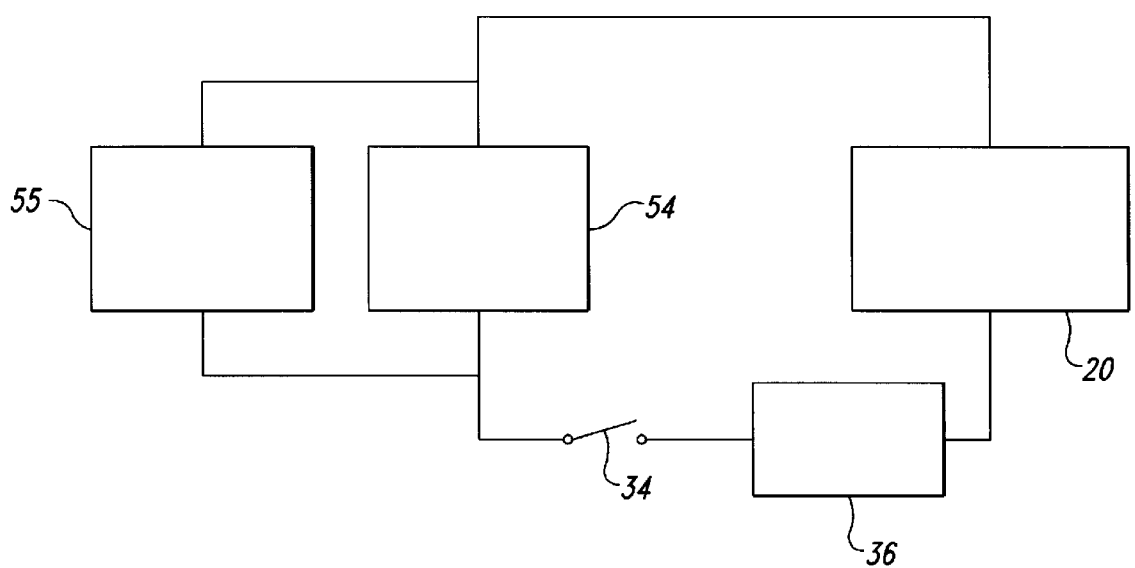

There are various possibilities with regard to the disposition of the power supply which is shown in the hard-wire diagram of FIG. 6. A battery charger 55, battery 54, compressor 20, fail-safe 36 and switch 34 are represented. Charger 55 could be replaced by either a 12 volt adaptor, an A.C. adaptor, or plug which could also complete the circuit.

In operation of the nasal inhalation device, the device of the present invention is capable of providing a nebulized liquid and medication to an individual 60 as follows.

In setting up the nasal inhalation device, individual 60 would place a predetermined quantity of the contents of a dose applicator means (not shown) into a nebulizing outlet 24*c* which emerges through opening 25 in a shell 58. The liquid or medication then becomes contained within a nebulizing device reservoir 24*b*.

One then connects one end of a nasal tubing 28 to nebulizing outlet 24*c* and the other end of tubing 28 in the nostrils of individual 60 receiving treatment. Ideally such tubing would be manufactured of reusable, #1, #2 or suitably recyclable plastic.

Finally, the device is connected to a source of electrical energy by any of a plurality of standard means including a standard plug, 12 V adaptor, A.C. adaptor or a battery 54.

The device is then ready for use.

The individual may then proceed with the treatment as needed. This may be done while individual is stationary or active. In one embodiment this is permitted by utilizing lightweight construction and small size, capable of fitting in a handbag or coat pocket. In one embodiment shell 58 fitted with removable clip 46 allows for attachment to individual's waistband or article. Ideally shell 58 is constructed of impact and heat-resistant material. Furthermore in one embodiment a convertible carrying case 42 can be adapted for shoulder or fanny wear, leaving the hands of individual 60 free during use. Carrying case 42 would ideally be manufactured of soft, cushioned material, its straps fitted with fanny pack conversion attaching fasteners 49*a*, and provided with a plurality of pivot points 49*b* about which convertible straps 49 can pivot to provide support needed for fanny pack configuration. The carrying case provides access to nebulizer 24 and switch 34.

Operation of the nasal inhalation device begins with activation of compressor 20 by activating a control switch 34 and in one embodiment a fail-safe 36. Such fail-safe ideally would be built-in to switch 34.

Compressor 20 begins to run causing intake of ambient air through an air filter 42, and a compressor inlet 20*b*, producing output of pressurized air flow through a compressor outlet 20*c*, into a conduit 22, which is connected to a pump means 20*d* of compressor 20. Such connections are in the form of one-way valves to prevent back-flow of air from compressor or conduit.

In one embodiment a regulator 26 would permit changes in pressure of air supplied to nebulizer to suit a variety of treatment needs. The individual turns a regulator dial, switch or button means 26*a* to adjust air flow for different applications that may be indicated.

Air flow continues through conduit 22, connecting to a nebulizing inlet 24*a* where the incoming air from compressor 20 entering through inlet 24*a* causes the liquid and medication contained in nebulizing reservoir 24*b* to be reduced to a fine spray. Ideally the nebulizing device 24 would allow formation of nebulized particles of a predetermined size to be formed. It is desirable to maintain uniform size and distribution of nebulized particles because different particle size is associated with varying penetration and distribution.

The spray of liquid and medication passes from nebulizing reservoir 24*b*, through nebulizing outlet 24*c* connecting to nasal tubing 28. In one embodiment this connection would consist of a "male quick connect" although other means of attachment including screw-on or snap-on could be utilized. Finally the spray of liquid passes through nasal tubing 28 to individual 60.

In one embodiment nebulizing outlet 24*c* is also adaptable to accept an oral tubing 30 and a face-mask tubing 32 as shown in FIGS. 2*b* and 2*c*.

It is preferred that air supplied by compressor 20 be filtered prior to use in nebulizing device 24. Such filtration may be provided by using a filter 42 as illustrated in FIG. 4.

Modifications may be made in the therapeutic inhalation device of the present invention without departing from its spirit or purpose.

The foregoing elements are electrically connected in the manner diagrammatically shown in FIG. 6.

Essentially compressor 20 and battery 54 are directly connected to each other, however interposed between those elements, in series connection, is provided switch 34 and fail-safe 36. Switch 34 is used as the master switch which operates compressor 20 and therefore the nasal inhalation device.

As illustrated in FIG. 3 switch 34 extends through shell 58 to permit actuation of the switch. Although such positioning of switch 34 is not essential, it is shown in FIG. 3 to illustrate that the individual carrying the device by clip 46 is able to operate switch 34 easily and quickly from that position. In fact, the individual is able to switch the device on and off as needed, without having to adjust or remove the device. Furthermore, the recessed position of the switch in the embodiment shown in FIG. 3 helps to prevent inadvertent activation of the switch. In another embodiment (not shown) positioning switch 34 under a lid 44 would also reduce the potential for accidentally activating or de-activating the inhalation device, which could adversely effect the power available from battery 54 for operation of the device.

Since the device of the present invention is intended for use while individual is in any position, indoors or outdoors, away from external sources of power, it is essential that the individual be assured that the battery will maintain sufficient power to operate the system as needed. Consequently, in addition to positioning switch 34 as above described, it is also preferred, although not required to provide fail-safe 36 which is capable of preventing unwanted accidental operation of the device, which could adversely affect the power available from battery 54.

Also represented in FIG. 6 is a battery charging means 55. Such charging means could be omitted from the system of the present invention, however, its inclusion is preferred so that a means for recharging battery 54 is always available to individual 60. A plurality of charging means can be utilized such as by way of a 12 volt adaptor, A.C. adaptor, removable, rechargeable battery 54 with either a separate charger, or a device charging or docking base.

Operation of the device is controlled by switch 34. If fail safe 36 is made part of the device, the fail-safe 36 would also have to be actuated, to complete the circuit of FIG. 6.

It may therefore be seen that the above disclosed invention serves well to accomplish the objects previously stated.

It may also be seen that the above described invention may be embodied in other specific forms in addition to those above disclosed and therefore the disclosure made should be interpreted in an illustrative and not a limiting sense.

Thus the reader will see that the nasal inhalation device of the invention provides a highly effective, reliable, lightweight, yet economical device which is simple to operate and which can be used by persons of any age, regardless of disease or physical limitations.

In addition, the device is re-usable, with a life expectancy in the range of about five years. The device utilizes an economical, re-usable and ideally recyclable nebulizing device and tubing means and in one embodiment is adaptable to accept a solar means of power. Furthermore, the device has the additional advantage of utilizing a variety of readily adaptable medications that are already approved for nasal administration and that are widely available both over the counter and by prescription. Therefore, the reader will agree that the nasal inhalation device of the invention provides a device which has the advantage of being environmentally responsible, economical to manufacture, purchase and operate.

While my above description contains many specificities, these should not be construed as limitations of the scope of the invention, but rather as merely providing illustrations of some of the embodiments of this invention. Many other variations are possible. For example the shell can be produced in a multitude of colors, including neon, transparent, and in a variety of motifs. The soft carrying case, tubing and nebulizing device can be produced in a multitude of colors and motifs. The device can have other sizes and shapes, including cylindrical, beveled, spherical, pyramidal. The device can be adaptable to deliver treatments orally and by face-mask for targeting the lower respiratory tract. In one embodiment, the tubing can consist of two parts, comprising the main tubing and the delivery tip that combine by an air tight connection, or adapting means. The individual can then use the delivery tips as needed interchangeably, such as in the presence of coexisting asthma or other lower respiratory condition and rhinitis or other upper respiratory condition.

Figure 3A:
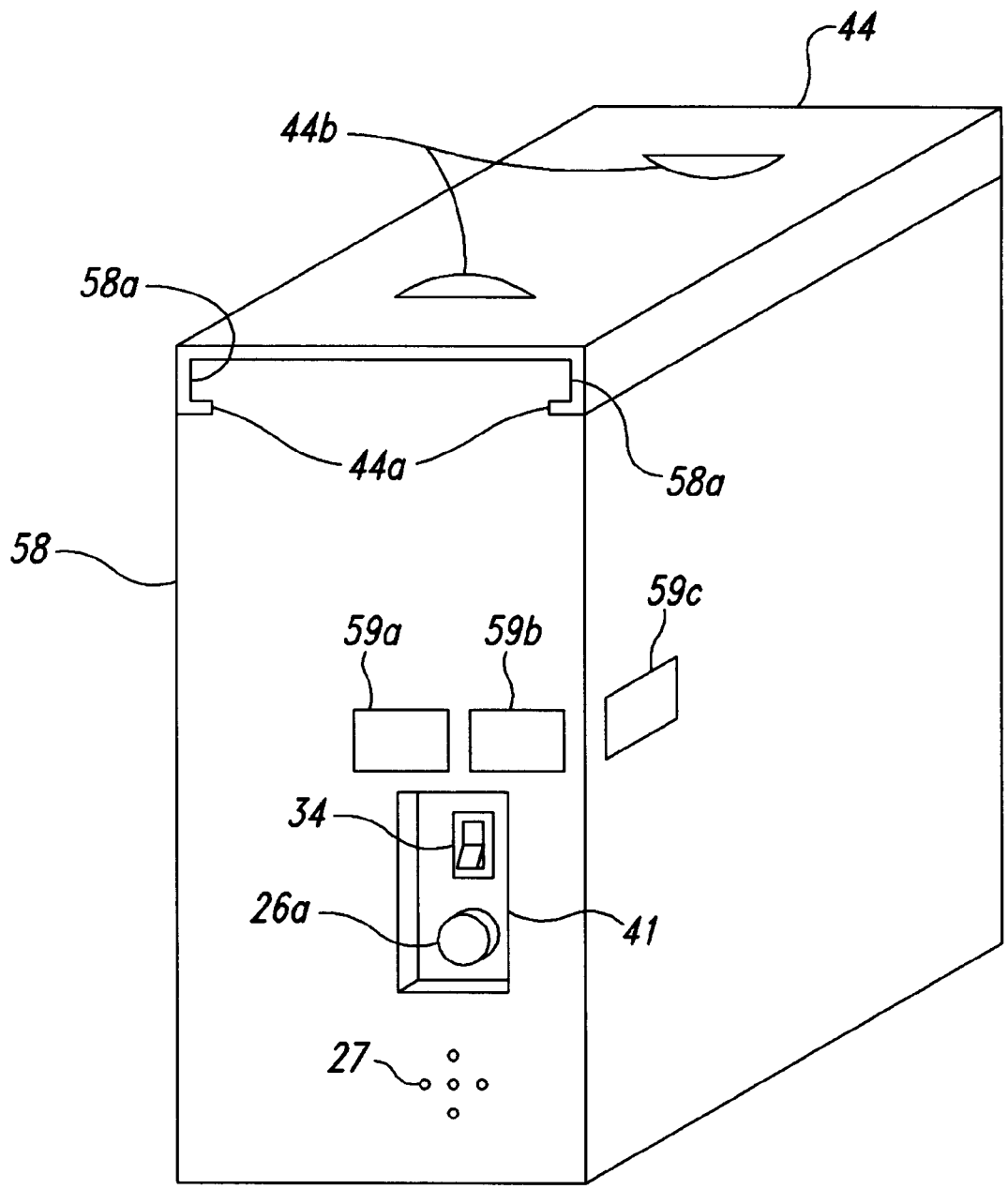
Figure 3B:
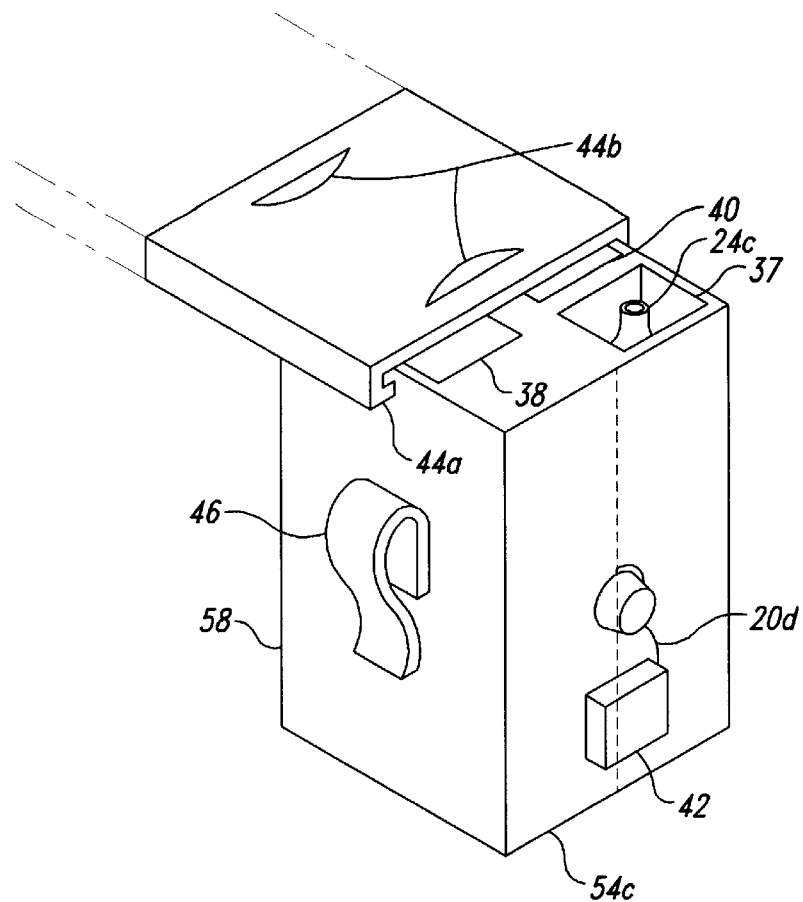
Figure 3C:
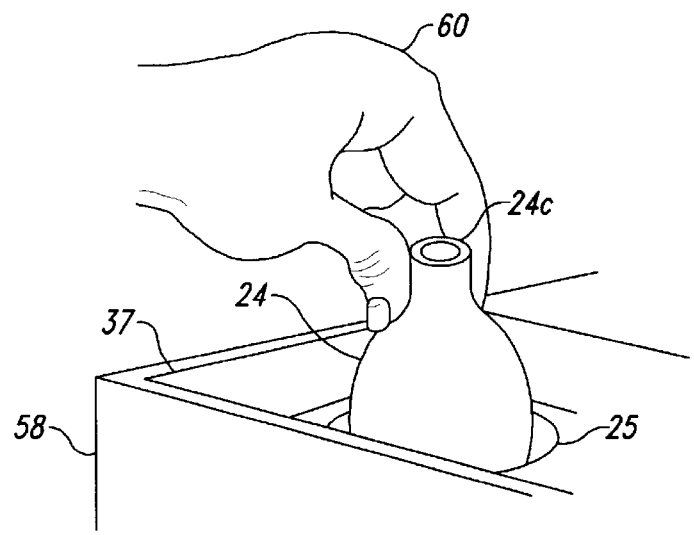
Figure 3D:
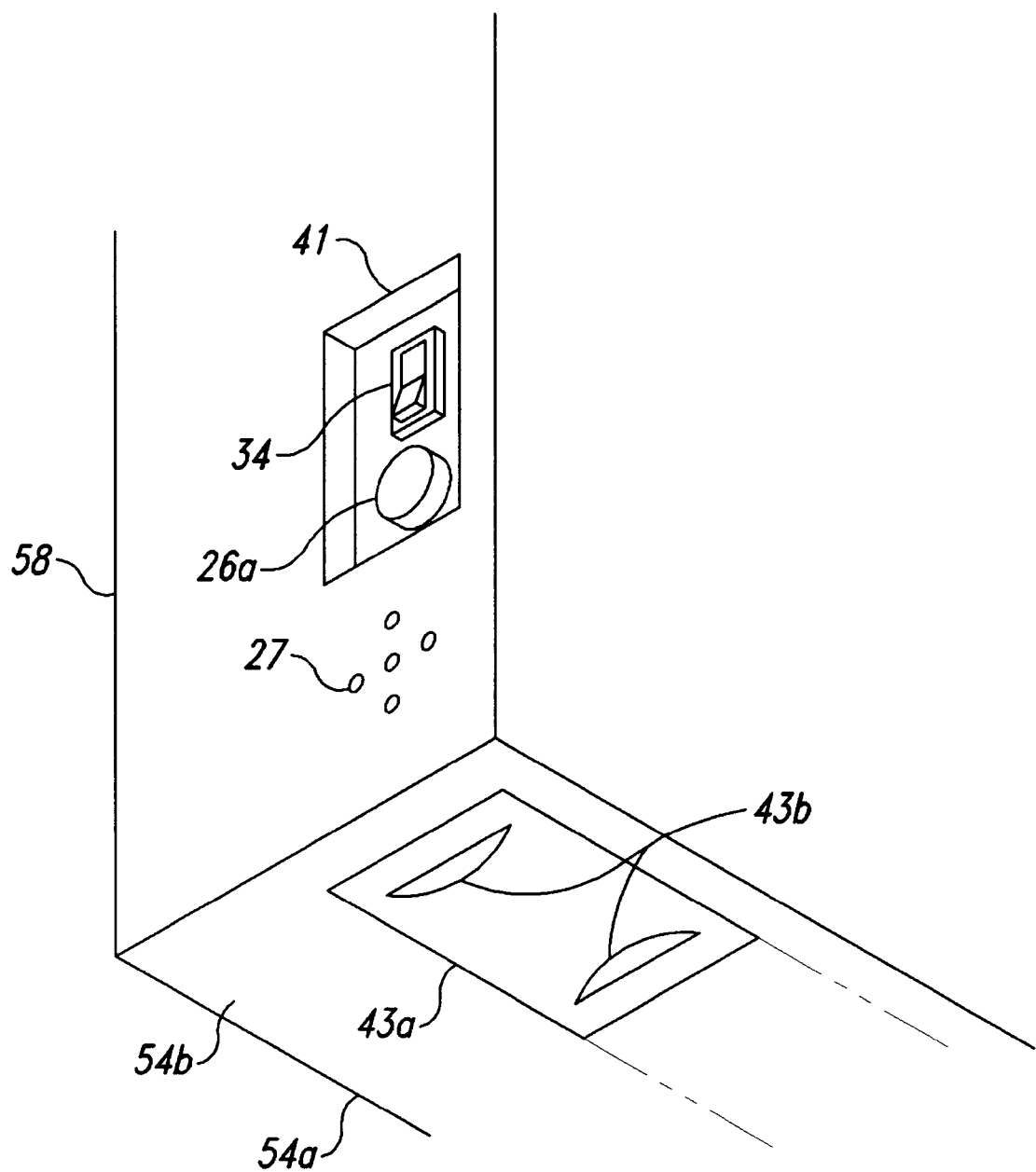
Figure 4:
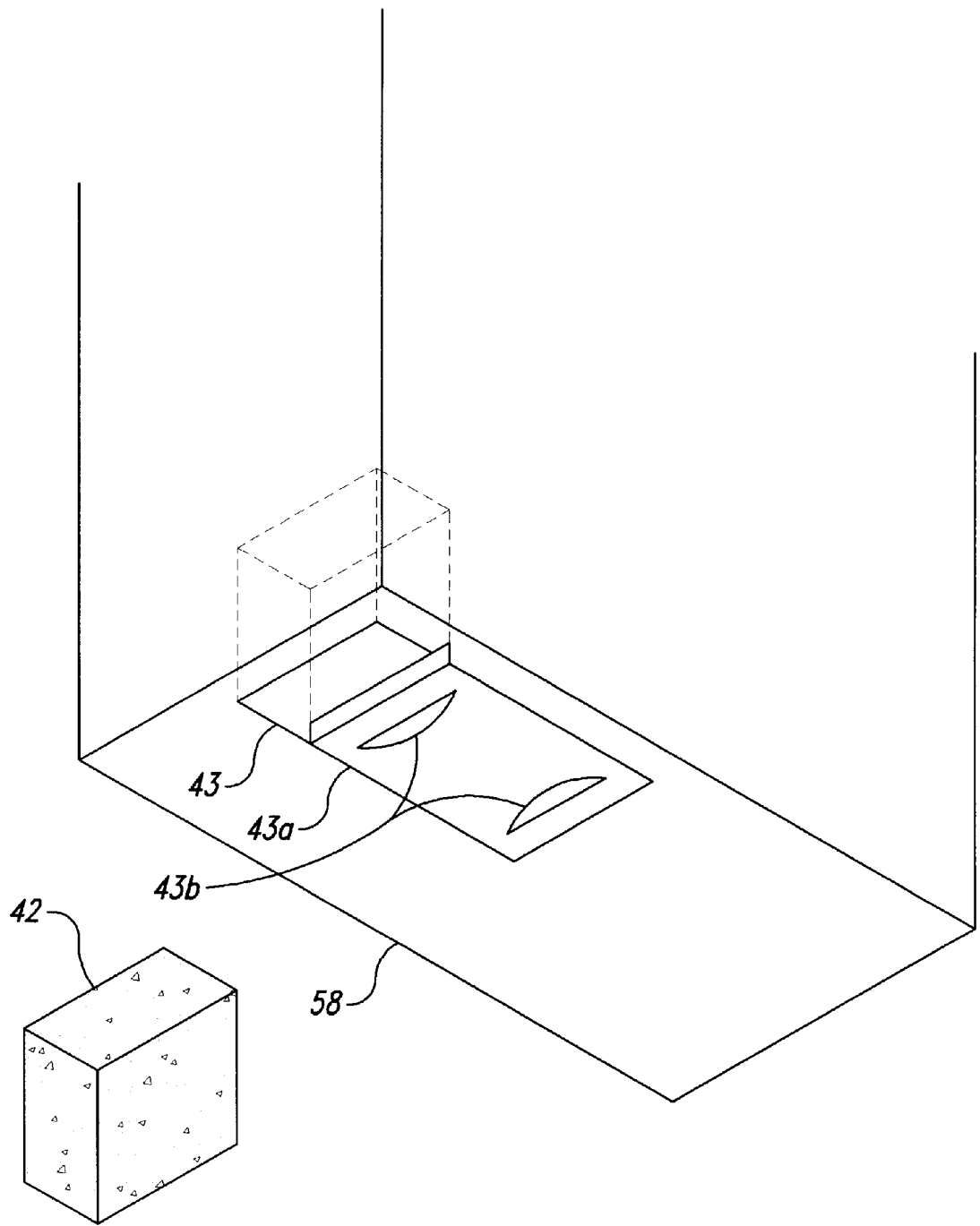

Furthermore, in one embodiment the battery status can be monitored by visual or audible signal externally displayed or emitted from the device. Similarly, the device can have a built-in mechanism for sensing the emptying of the nebulizer reservoir, thus indicating the end of the treatment, and can then signal the individual by a variety of methods, such as audible, visual or vibratory means, shown in FIG. 3A as 59a, 59b, and 59c, respectively. In addition, once the end of treatment is recognized, the device can automatically deactivate.

In addition, the device of the present invention allows the individual to comfortably and freely inhale a set concentration and volume of nebulized liquid and medication over several minutes through the course of the natural breathing process resulting in effective distribution of the treatment spray to the upper respiratory tract.

Accordingly, the scope of the invention should be determined not by the embodiments illustrated, but by the appended claims and their legal equivalents.

I claim:

1. A portable human nasal inhalation therapy device, comprising:

a housing sized to be worn by a human user;

an internal electrically powered compressor received by the housing and having an input of ambient air for producing a pressurized air output, the compressor being sized to be supported by the user while the compressor is in use;

an internal conduit having inlet and outlet ends, the inlet end being connected to and receiving the output of the compressor;

a nebulizing device at least partially housed within the housing when the nebulizing device is in use, the nebulizing device having an inlet removably connected to the outlet end of said conduit, the nebulizing device being sized to be supported by the user while the nebulizing device is in use, the nebulizing device including a removable reservoir for holding a liquid or medication used in inhalation therapy, the nebulizing device being configured to reduce the medication in the reservoir to a fine spray by the interaction with the pressurized air flow from the compressor to treat nasal, upper respiratory, and other conditions; and external tubing for delivering the spray from an outlet of the nebulizing device to the user's nasal passages, the tubing being bifurcated and including two openings, each sized to fit within one of the user's nostrils, further wherein an outer diameter of the external tubing proximate each opening is larger than a diameter of the external tubing at a location spaced apart from the openings and being shaped to remain in place in the user's nostril and provide the user with therapeutic treatment of nasal, upper respiratory, and other conditions treatable by intra-nasal administration of medication.

2. The apparatus of claim 1, further comprising the liquid, wherein said liquid is selected from the group consisting of substantially water and substantially saline.

3. The apparatus of claim 1, further comprising the medication, wherein the medication is selected from the group consisting of anti-histamines, antibiotics, steroidal and non-steroidal anti-inflammatory agents, sympathomimetic amines, mast cell stabilizers, moisturizing agents, mucolytic agents, anti-cholinergic agents, decongestants, anesthetics, analgesics, and anti-viral agents.

4. The device of claim 1, further including a removable clip for carrying the device on the user or as a personal item.

5. The device of claim 1 further including a soft carrying case.

6. The device of claim 5 wherein the carrying case has built-in access to a switch, regulator control means, an air intake and the nebulizing device.

7. The device of claim 5 wherein the carrying case is adaptable for carrying by shoulder and fanny method.

8. The device of claim 1 wherein the external tubing includes self-retaining nasal tubing, where the nasal tubing is bifurcated and includes two openings, each sized to fit within one of the user's nostrils, further wherein an outer diameter of the external tubing proximate each opening is larger than a diameter of the external tubing at a location spaced apart from the openings so as to remain in place in the user's nostril.

9. The device of claim 1, further comprising an electrical source for said compressor selected from the group consisting of:

a. rechargeable battery,
   b. A. C. adaptor,
   c. 12 volt adaptor,
   d. solar adaptor, and
   e. standard plug.

10. The device of claim 1 further including an adjustable regulator to control air flow to the nebulizer.

11. The device of claim 1 wherein the nebulizer is removable.

12. The device of claim 1 further including compartments for medication or fluid, and tubing.

13. The device of claim 1 further, including an alerting system for monitoring energy, power and treatment status, comprising alerting means selected from the group consisting of audible means, visual means, and vibratory means.

14. The device of claim 1 further including a pre-compressor filter.

15. The device of claim 14 wherein said filter is located in an easily accessible compartment in communication with the compressor's air intake.

16. A method for treating various nasal and upper respiratory conditions comprising the steps of:

placing a liquid or medication into a nebulizing device;

connecting one end of a tubing means to an output end of said nebulizing device;

inserting another end of said tubing means into an individual's nasal passages;

electrically activating compressor means to supply air under pressure to the nebulizing device to deliver a fine spray of liquid or liquid medication to the nasal passages of the individual over a period of several minutes;

supporting said nebulizer and said compressor with the individual's body while delivering the fine spray of liquid and liquid medication; and removing at least a portion of the nebulizer from a housing supporting the nebulizer to refill the nebulizer with a liquid or medication.

17. The treatment method of claim 16 wherein particle size in the spray of liquid and liquid medication is substantially from about 1 micron to substantially about 5 microns in diameter.

18. The treatment method of claim 16, further including regulating air flow from the compressor means to the nebulizing device.

19. The treatment method of claim 18, further comprising regulating the air flow to be between about 2 liters per minute and about 15 liters per minute.

20. A portable human nasal inhalation therapy device, comprising:

a housing sized to be worn by a human user;

an electrically powered compressor located at least partially within the housing, the compressor having an air intake to receive ambient air and an air outlet to deliver compressed air, the compressor being sized to be readily supported by the user while the compressor is in use;

a conduit having first and second opposite ends, the first end being connected to the air outlet of the compressor to receive the compressed air;

an atomizer having an inlet and an outlet, the inlet being connected to the second end of the conduit, the atomizer further having a removable reservoir to receive liquid having medication, the atomizer being configured to atomize the liquid by combining the liquid with the compressed air from the compressor to form a fine spray, the atomizer being sized to be supported by the user while the atomizer is in use;

a tube extending at least partially outside the housing and having a first end coupled to the outlet of the atomizer and a second end opposite the first end, the second end being configured to fit within or near to a human nostril to deliver the spray to a human nasal passage; and a portable power supply coupled to the compressor to power the compressor while the compressor is supported by the user.

21. The device of claim 20 wherein the portable power supply includes a rechargeable battery.

22. The device of claim 20 wherein the portable power supply includes a recharging device.

23. The device of claim 20, further comprising a clip removably attached to the housing and configured to be worn by the user to support the compressor and atomizer when the compressor and atomizer are in use.

24. The device of claim 20 wherein the second end of the tubing includes tubing stays configured to engage an inner surface of the nasal passage and restrict motion of the tubing away from the nasal passage.

* * * * *

UNITED STATES PATENT AND TRADEMARK OFFICE
CERTIFICATE OF CORRECTION

PATENT NO. : 6,076,520
DATED : June 20, 2000
INVENTOR(S) : Emily L. Cooper

It is certified that error appears in the above-identified patent and that said Letters Patent is hereby corrected as shown below:

Column 7,
Line 64, following "user" insert -- during use --.

Column 8,
Line 9, following "of" delete "said" and insert -- the --.
Line 16, following "compressor" delete "to treat nasal, upper respiratory, and other conditions" and insert -- for intra-nasal administration --.
Line 26, following "and" delete "being shaped" and insert -- is sized to frictionally engage internal walls of the nostril, --.
Line 27, following "treatment" delete "of nasal, upper respiratory, and other conditions treatable".

Column 9,
Line 18, delete "said" and insert -- the --.
Line 19, following "of" delete "said" and insert -- the --.
Line 20, following "passages" insert -- and frictionally engaging enlarged portions of the tubing means with internal wall of the nasal passages --.
Line 21, following "activating" insert -- a --.
Line 21, following "compressor" delete "means".
Line 26, following "supporting" delete "said nebulizer" and insert -- the nebulizing device --.
Line 26, following "and" delete "said" and insert -- the --.
Line 29, following "the" delete "nebulizer" and insert -- nebulizing device --.
Line 30, twice on this line following "the" delete "nebulizer" and insert -- nebulizing device --.

UNITED STATES PATENT AND TRADEMARK OFFICE
CERTIFICATE OF CORRECTION

PATENT NO. : 6,076,520
DATED : June 20, 2000
INVENTOR(S) : Emily L. Cooper

It is certified that error appears in the above-identified patent and that said Letters Patent is hereby corrected as shown below:

Column 10,
Line 24, following "within" delete "or near to".
Line 24, following "nostril" insert -- the second end having an outer diameter sized to frictionally engage internal walls of the nostril and remain in place in the nostril without additional support. --

Signed and Sealed this

Twenty-fifth Day of September, 2001

Attest:

*Nicholas P. Godici*

NICHOLAS P. GODICI
*Attesting Officer*     *Acting Director of the United States Patent and Trademark Office*